(12) United States Patent
Syring et al.

(10) Patent No.: US 7,815,926 B2
(45) Date of Patent: Oct. 19, 2010

(54) IMPLANT FOR ARTICULAR CARTILAGE REPAIR

(75) Inventors: Carina Syring, Biel-Benken (CH); Rudiger Walter Arthur von Versen, Wandlitz (DE)

(73) Assignee: Musculoskeletal Transplant Foundation, Edison, NJ (US)

( * ) Notice: Subject to any disclaimer, the term of this patent is extended or adjusted under 35 U.S.C. 154(b) by 634 days.

(21) Appl. No.: 11/481,955

(22) Filed: Jul. 7, 2006

(65) Prior Publication Data
US 2007/0009610 A1 Jan. 11, 2007

Related U.S. Application Data

(60) Provisional application No. 60/697,563, filed on Jul. 11, 2005.

(51) Int. Cl.
*A61F 2/00* (2006.01)
*C12N 5/07* (2010.01)
*C12N 11/14* (2010.01)
*C12N 11/10* (2010.01)

(52) U.S. Cl. .................. 424/423; 424/93.7; 435/176; 435/178

(58) Field of Classification Search .......... None
See application file for complete search history.

(56) References Cited

U.S. PATENT DOCUMENTS

| | | | |
|---|---|---|---|
| 3,400,199 A | 9/1968 | Balassa | |
| 3,551,560 A | 12/1970 | Theile | |
| 3,772,432 A | 11/1973 | Balassa | |
| 3,867,728 A | 2/1975 | Stubstad et al. | |
| 4,060,081 A | 11/1977 | Yannas et al. | |
| 4,172,128 A | 10/1979 | Thiele et al. | |
| 4,201,845 A | 5/1980 | Feder et al. | |
| 4,296,100 A | 10/1981 | Franco | |
| 4,378,347 A | 3/1983 | Franco | |
| 4,394,370 A | 7/1983 | Jefferies | |
| 4,400,833 A | 8/1983 | Kurland | |
| 4,442,655 A | 4/1984 | Stroetmann | |
| 4,458,678 A | 7/1984 | Yannas et al. | |
| 4,479,271 A | 10/1984 | Bolesky et al. | |
| 4,501,269 A | 2/1985 | Bagby | |
| 4,505,266 A | 3/1985 | Yannas et al. | |
| 4,600,574 A | 7/1986 | Lindner et al. | |
| 4,627,853 A | 12/1986 | Campbell et al. | |
| 4,642,120 A * | 2/1987 | Nevo et al. ............... | 424/422 |
| 4,656,137 A | 4/1987 | Balassa | |
| 4,681,763 A | 7/1987 | Nathanson et al. | |
| 4,683,195 A | 7/1987 | Mullis et al. | |
| 4,683,202 A | 7/1987 | Mullis | |
| 4,757,017 A | 7/1988 | Cheung | |
| 4,776,173 A | 10/1988 | Kamarei et al. | |
| 4,776,853 A | 10/1988 | Klement et al. | |
| 4,795,467 A | 1/1989 | Piez et al. | |
| 4,801,299 A | 1/1989 | Brendel et al. | |
| 4,837,379 A | 6/1989 | Wienberg | |
| 4,846,835 A | 7/1989 | Grande | |
| 4,880,429 A | 11/1989 | Stone | |
| 4,902,508 A | 2/1990 | Badylak et al. | |
| 4,904,259 A | 2/1990 | Itay | |
| 4,932,973 A | 6/1990 | Gendler | |
| 4,950,296 A | 8/1990 | McIntyre | |
| 4,950,483 A | 8/1990 | Ksander et al. | |
| 4,955,911 A | 9/1990 | Frey et al. | |
| 4,963,146 A | 10/1990 | Li | |
| 4,965,188 A | 10/1990 | Mussis et al. | |
| 4,971,954 A | 11/1990 | Brodsky et al. | |
| 4,976,738 A | 12/1990 | Frey et al. | |
| 4,978,355 A | 12/1990 | Frey et al. | |
| 4,994,559 A | 2/1991 | Moscatelli et al. | |
| 5,002,583 A | 3/1991 | Pitaru et al. | |
| 5,007,934 A | 4/1991 | Stone | |

(Continued)

FOREIGN PATENT DOCUMENTS

EP 0517030 A2 12/1992

(Continued)

OTHER PUBLICATIONS

Ornitz et al., "Protein Family Review: Fibroblast Growth Factors", Genome Biology (2001) 2(3): reviews 3005.1-3005.12, http://genomebiology.com/2001/2/3/reviews/3005.1.

(Continued)

*Primary Examiner*—David M Naff
(74) *Attorney, Agent, or Firm*—Greenberg Traurig, LLP

(57) ABSTRACT

An implant for articular cartilage repair includes (1) a three-dimensional body formed of cancellous bone having a demineralized section that contains bone morphogenetic proteins (BMP's) that are released by the demineralization but retained in the body, and (2) a cartilage layer formed on a surface of the demineralized section. The cartilage layer is formed by a method including the steps of (a) isolating chondrocytes from articular cartilage of a donor; (b) cultivating the isolated chondrocytes in a medium; (c) suspending the cultivated chondrocytes in agarose; (d) adding the cultivated chondrocytes to the demineralized section of the body, whereby the cultivated chondrocytes are stimulated by the BMP's retained in the body; and (e) incubating the cultivated chondrocytes to form a plurality of layers of chondrocytes on the demineralized section, wherein the plurality of layers of chondrocytes forms the cartilage layer.

19 Claims, 1 Drawing Sheet

U.S. PATENT DOCUMENTS

| | | |
|---|---|---|
| 5,041,138 A | 8/1991 | Vacanti et al. |
| 5,053,049 A | 10/1991 | Campbell |
| 5,053,050 A | 10/1991 | Itay |
| 5,067,964 A | 11/1991 | Richmond et al. |
| 5,073,373 A | 12/1991 | O'Leary et al. |
| 5,084,051 A | 1/1992 | Tormala et al. |
| 5,118,512 A | 6/1992 | O'Leary et al. |
| 5,152,791 A | 10/1992 | Hakamatsuka et al. |
| 5,155,214 A | 10/1992 | Baird et al. |
| 5,191,067 A | 3/1993 | Lappi et al. |
| 5,195,892 A | 3/1993 | Gersberg |
| 5,206,023 A | 4/1993 | Hunziker |
| 5,236,456 A | 8/1993 | O'Leary et al. |
| 5,256,140 A | 10/1993 | Fallick |
| 5,260,420 A | 11/1993 | Burnouf-Radosevich et al. |
| 5,266,476 A | 11/1993 | Sussman et al. |
| 5,270,300 A | 12/1993 | Hunziker |
| 5,275,826 A | 1/1994 | Badylak et al. |
| 5,284,155 A | 2/1994 | Treadwell et al. |
| 5,290,558 A | 3/1994 | O'Leary et al. |
| 5,298,254 A | 3/1994 | Prewett et al. |
| 5,302,702 A | 4/1994 | Seddon et al. |
| 5,306,304 A | 4/1994 | Gendler |
| 5,306,311 A | 4/1994 | Stone et al. |
| 5,310,883 A | 5/1994 | Seddon et al. |
| 5,314,476 A | 5/1994 | Prewett et al. |
| 5,326,357 A | 7/1994 | Kandel |
| 5,329,846 A | 7/1994 | Bonutti |
| 5,336,616 A | 8/1994 | Livesey et al. |
| 5,338,772 A | 8/1994 | Bauer et al. |
| 5,352,463 A | 10/1994 | Badylak et al. |
| 5,354,557 A | 10/1994 | Oppermann et al. |
| 5,356,629 A | 10/1994 | Sander et al. |
| 5,368,858 A | 11/1994 | Hunziker |
| 5,380,328 A | 1/1995 | Morgan |
| 5,411,885 A | 5/1995 | Marx |
| 5,425,769 A | 6/1995 | Snyders, Jr. |
| 5,439,684 A | 8/1995 | Prewett et al. |
| 5,439,818 A | 8/1995 | Fiddes et al. |
| 5,443,950 A | 8/1995 | Naughton et al. |
| 5,464,439 A | 11/1995 | Gendler |
| 5,466,462 A | 11/1995 | Rosenthal et al. |
| 5,491,220 A | 2/1996 | Seddon et al. |
| 5,496,722 A | 3/1996 | Goodwin et al. |
| 5,507,813 A | 4/1996 | Dowd et al. |
| 5,512,460 A | 4/1996 | Nauro et al. |
| 5,513,662 A | 5/1996 | Morse et al. |
| 5,516,532 A | 5/1996 | Atala et al. |
| 5,545,222 A | 8/1996 | Bonutti |
| 5,556,430 A | 9/1996 | Gendler |
| 5,569,272 A | 10/1996 | Reed et al. |
| 5,571,895 A | 11/1996 | Kurokawa et al. |
| 5,576,288 A | 11/1996 | Lappi et al. |
| 5,604,293 A | 2/1997 | Fiddes et al. |
| 5,607,474 A | 3/1997 | Athanasiou et al. |
| 5,614,496 A | 3/1997 | Dunstan et al. |
| 5,622,928 A | 4/1997 | Naruo et al. |
| 5,624,463 A | 4/1997 | Stone et al. |
| 5,631,011 A | 5/1997 | Wadstrom |
| 5,632,745 A | 5/1997 | Schwartz |
| 5,656,598 A | 8/1997 | Dunstan et al. |
| 5,662,710 A | 9/1997 | Bonutti |
| 5,679,637 A | 10/1997 | Lappi et al. |
| 5,695,998 A | 12/1997 | Badylak et al. |
| 5,700,476 A | 12/1997 | Rosenthal et al. |
| 5,700,774 A | 12/1997 | Hattersley et al. |
| 5,707,962 A | 1/1998 | Chen et al. |
| 5,713,374 A | 2/1998 | Pachence et al. |
| 5,716,413 A | 2/1998 | Walter et al. |
| 5,723,331 A | 3/1998 | Tubo et al. |
| 5,736,372 A | 4/1998 | Vacanti et al. |
| 5,749,874 A | 5/1998 | Schwartz |
| 5,759,190 A | 6/1998 | Vibe-Hansen et al. |
| 5,769,899 A | 6/1998 | Schwartz et al. |
| 5,770,417 A | 6/1998 | Vacanti et al. |
| 5,782,835 A | 7/1998 | Hart et al. |
| 5,782,915 A | 7/1998 | Stone |
| 5,786,217 A | 7/1998 | Tubo et al. |
| 5,800,537 A | 9/1998 | Bell |
| 5,814,084 A | 9/1998 | Grivas et al. |
| 5,842,477 A | 12/1998 | Naughton et al. |
| 5,846,931 A | 12/1998 | Hattersley et al. |
| 5,853,746 A | 12/1998 | Hunziker |
| 5,855,620 A | 1/1999 | Bishopric et al. |
| 5,859,208 A | 1/1999 | Fiddes et al. |
| 5,863,296 A | 1/1999 | Orton |
| 5,863,297 A | 1/1999 | Walter et al. |
| 5,866,415 A | 2/1999 | Villeneuve |
| 5,876,452 A | 3/1999 | Athanasiou et al. |
| 5,888,219 A | 3/1999 | Bonutti |
| 5,893,888 A | 4/1999 | Bell |
| 5,899,936 A | 5/1999 | Goldstein |
| 5,899,939 A | 5/1999 | Boyce et al. |
| 5,904,716 A | 5/1999 | Gendler |
| 5,906,827 A | 5/1999 | Khouri et al. |
| 5,910,315 A | 6/1999 | Stevenson et al. |
| 5,916,265 A | 6/1999 | Hu |
| 5,948,429 A | 9/1999 | Bell et al. |
| 5,955,438 A | 9/1999 | Pitaru et al. |
| 5,964,805 A | 10/1999 | Stone |
| 5,972,368 A | 10/1999 | McKay |
| 5,972,385 A | 10/1999 | Liu et al. |
| 5,974,663 A | 11/1999 | Ikeda et al. |
| 5,989,269 A | 11/1999 | Vibe-Hansen et al. |
| 5,989,289 A | 11/1999 | Coates et al. |
| 5,989,866 A | 11/1999 | Deisher et al. |
| 5,998,170 A | 12/1999 | Arakawa et al. |
| 6,001,352 A | 12/1999 | Boyan et al. |
| 6,005,161 A | 12/1999 | Brekke et al. |
| 6,013,853 A | 1/2000 | Athanasiou et al. |
| 6,017,348 A | 1/2000 | Hart et al. |
| 6,025,334 A | 2/2000 | Dupont et al. |
| 6,025,538 A | 2/2000 | Yaccarino, III |
| 6,027,743 A | 2/2000 | Khouri et al. |
| 6,030,635 A | 2/2000 | Gertzman et al. |
| 6,037,171 A | 3/2000 | Larsson |
| 6,039,762 A | 3/2000 | McKay |
| 6,060,640 A | 5/2000 | Pauley et al. |
| 6,074,663 A | 6/2000 | Delmotte et al. |
| 6,080,194 A | 6/2000 | Pachence et al. |
| 6,090,996 A | 7/2000 | Li |
| 6,090,998 A | 7/2000 | Grooms et al. |
| 6,096,081 A | 8/2000 | Grivas et al. |
| 6,096,347 A | 8/2000 | Geddes et al. |
| 6,110,209 A | 8/2000 | Stone |
| 6,110,482 A | 8/2000 | Khouri et al. |
| 6,123,731 A | 9/2000 | Boyce et al. |
| 6,132,472 A | 10/2000 | Bonutti |
| 6,143,293 A | 11/2000 | Weiss et al. |
| 6,156,068 A | 12/2000 | Walter et al. |
| 6,165,486 A | 12/2000 | Marra et al. |
| 6,165,487 A | 12/2000 | Ashkar et al. |
| 6,180,605 B1 | 1/2001 | Chen et al. |
| 6,183,737 B1 | 2/2001 | Zaleske et al. |
| 6,189,537 B1 | 2/2001 | Wolfinbarger, Jr. |
| 6,197,586 B1 | 3/2001 | Bhatnagar et al. |
| 6,200,347 B1 | 3/2001 | Anderson et al. |
| 6,221,854 B1 | 4/2001 | Radomsky |
| 6,231,607 B1 | 5/2001 | Ben-Bassat et al. |
| 6,242,247 B1 | 6/2001 | Rieser et al. |
| 6,251,143 B1 | 6/2001 | Schwartz et al. |
| 6,258,778 B1 | 7/2001 | Rodgers et al. |
| 6,261,586 B1 | 7/2001 | McKay |
| 6,267,786 B1 | 7/2001 | Stone |

| | | | | | | |
|---|---|---|---|---|---|---|
| 6,270,528 B1 | 8/2001 | McKay | | 6,712,851 B1 | 3/2004 | Lemperle et al. |
| 6,274,090 B1 | 8/2001 | Coelho et al. | | 6,727,224 B1 | 4/2004 | Zhang et al. |
| 6,274,663 B1 | 8/2001 | Hosokawa et al. | | 6,730,314 B2 | 5/2004 | Jeschke et al. |
| 6,274,712 B1 | 8/2001 | Springer et al. | | 6,734,018 B2 | 5/2004 | Wolfinbarger, Jr. et al. |
| 6,280,473 B1 | 8/2001 | Lemperle et al. | | 6,743,232 B2 | 6/2004 | Overaker et al. |
| 6,281,195 B1 | 8/2001 | Rueger et al. | | 6,752,834 B2 | 6/2004 | Geistlich et al. |
| 6,283,980 B1 | 9/2001 | Vibe-Hansen et al. | | 6,761,739 B2 | 7/2004 | Shepard |
| 6,293,970 B1 | 9/2001 | Wolfinbarger, Jr. | | 6,761,887 B1 | 7/2004 | Kavalkovich et al. |
| 6,294,187 B1 | 9/2001 | Boyce et al. | | 6,767,369 B2 | 7/2004 | Boyer et al. |
| 6,294,359 B1 | 9/2001 | Fiddes et al. | | 6,776,800 B2 | 8/2004 | Boyer, II et al. |
| 6,303,585 B1 | 10/2001 | Spiro et al. | | 6,783,712 B2 | 8/2004 | Slivka et al. |
| 6,305,379 B1 | 10/2001 | Wolfinbarger, Jr. | | 6,808,585 B2 | 10/2004 | Boyce et al. |
| 6,306,174 B1 | 10/2001 | Gie et al. | | 6,815,416 B2 | 11/2004 | Carney et al. |
| 6,306,424 B1 | 10/2001 | Vyakamam et al. | | 6,838,440 B2 | 1/2005 | Stiles |
| 6,310,267 B1 | 10/2001 | Rapp | | 6,841,150 B2 | 1/2005 | Halvorsen et al. |
| 6,319,712 B1 | 11/2001 | Meenen et al. | | 6,852,114 B2 | 2/2005 | Cerundolo |
| 6,333,029 B1 | 12/2001 | Vyakarnam et al. | | 6,852,125 B2 | 2/2005 | Simon et al. |
| 6,352,558 B1 | 3/2002 | Spector | | 6,852,331 B2 | 2/2005 | Lai et al. |
| 6,352,971 B1 | 3/2002 | Deisher et al. | | 6,855,167 B2 | 2/2005 | Shimp et al. |
| 6,361,565 B1 | 3/2002 | Bonutti | | 6,855,169 B2 | 2/2005 | Boyer, II et al. |
| 6,376,244 B1 | 4/2002 | Atala | | 6,858,042 B2 | 2/2005 | Nadler et al. |
| 6,379,367 B1 | 4/2002 | Vibe-Hansen et al. | | 6,866,668 B2 | 3/2005 | Giannetti et al. |
| 6,379,385 B1 | 4/2002 | Kalas et al. | | 6,884,428 B2 | 4/2005 | Binette et al. |
| 6,383,221 B1 | 5/2002 | Scarborough et al. | | 6,890,354 B2 | 5/2005 | Steiner et al. |
| 6,387,693 B2 | 5/2002 | Reiser et al. | | 6,893,462 B2 | 5/2005 | Buskirk et al. |
| 6,398,811 B1 | 6/2002 | McKay | | 6,902,578 B1 | 6/2005 | Anderson et al. |
| 6,398,816 B1 | 6/2002 | Breitbart et al. | | 6,911,212 B2 | 6/2005 | Gertzman et al. |
| 6,398,972 B1 | 6/2002 | Blasetti et al. | | 6,932,977 B2 | 8/2005 | Heidaran et al. |
| 6,432,436 B1 | 8/2002 | Gertzman et al. | | 6,933,326 B1 | 8/2005 | Griffey et al. |
| 6,437,018 B1 | 8/2002 | Gertzman et al. | | 6,933,328 B2 | 8/2005 | Schacht |
| 6,440,141 B1 | 8/2002 | Philippon | | 6,949,252 B2 | 9/2005 | Mizuno et al. |
| 6,440,427 B1 | 8/2002 | Wadstrom | | 6,989,034 B2 | 1/2006 | Hammer et al. |
| 6,440,444 B2 | 8/2002 | Boyce et al. | | 6,995,013 B2 | 2/2006 | Connelly et al. |
| 6,454,811 B1 | 9/2002 | Sherwood et al. | | 7,009,039 B2 | 3/2006 | Yayon et al. |
| 6,458,144 B1 | 10/2002 | Morris et al. | | 7,018,416 B2 | 3/2006 | Hanson et al. |
| 6,458,158 B1 | 10/2002 | Anderson et al. | | 7,033,587 B2 | 4/2006 | Halvorsen et al. |
| 6,458,375 B1 | 10/2002 | Gertzman et al. | | 7,041,641 B2 | 5/2006 | Rueger et al. |
| 6,468,314 B2 | 10/2002 | Schwartz et al. | | 7,044,968 B1 | 5/2006 | Yaccarino, III et al. |
| 6,471,993 B1 | 10/2002 | Shastri et al. | | 7,045,141 B2 | 5/2006 | Merboth et al. |
| 6,475,175 B1 | 11/2002 | Rivera et al. | | 7,048,750 B2 | 5/2006 | Vibe-Hansen et al. |
| 6,486,377 B2 | 11/2002 | Rapp | | 7,048,762 B1 | 5/2006 | Sander et al. |
| 6,488,033 B1 | 12/2002 | Cerundolo | | 7,048,765 B1 | 5/2006 | Grooms et al. |
| 6,489,165 B2 | 12/2002 | Bhatnagar et al. | | 7,067,123 B2 | 6/2006 | Gomes et al. |
| 6,497,726 B1 | 12/2002 | Carter et al. | | 7,070,942 B2 | 7/2006 | Heidaran et al. |
| 6,503,277 B2 | 1/2003 | Bonutti | | 7,078,232 B2 | 7/2006 | Konkle et al. |
| 6,511,511 B1 | 1/2003 | Slivka et al. | | 7,108,721 B2 | 9/2006 | Huckle et al. |
| 6,511,958 B1 | 1/2003 | Atkinson et al. | | RE39,321 E | 10/2006 | MacPhee et al. |
| 6,514,514 B1 | 2/2003 | Atkinson et al. | | 7,115,146 B2 | 10/2006 | Boyer, II et al. |
| 6,520,964 B2 | 2/2003 | Tallarida et al. | | 7,125,423 B2 | 10/2006 | Hazebrouck |
| 6,530,956 B1 | 3/2003 | Mansmann | | 7,132,110 B2 | 11/2006 | Kay et al. |
| 6,534,084 B1 | 3/2003 | Vyakarnam et al. | | 7,137,989 B2 | 11/2006 | Asculai et al. |
| 6,541,024 B1 | 4/2003 | Kadiyala et al. | | 7,141,072 B2 | 11/2006 | Geistlich et al. |
| 6,548,729 B1 | 4/2003 | Seelich et al. | | 7,156,880 B2 | 1/2007 | Evans et al. |
| 6,569,172 B2 | 5/2003 | Asculai et al. | | 7,157,428 B2 | 1/2007 | Kusanagi et al. |
| 6,576,015 B2 | 6/2003 | Geistlich et al. | | 7,163,563 B2 | 1/2007 | Schwartz et al. |
| 6,582,960 B1 | 6/2003 | Martin et al. | | 7,166,133 B2 | 1/2007 | Evans et al. |
| 6,591,581 B2 | 7/2003 | Schmieding | | 7,179,299 B2 | 2/2007 | Edwards et al. |
| 6,592,598 B2 | 7/2003 | Vibe-Hansen et al. | | 7,182,781 B1 | 2/2007 | Bianchi et al. |
| 6,592,599 B2 | 7/2003 | Vibe-Hansen et al. | | 7,201,917 B2 | 4/2007 | Malaviya et al. |
| 6,599,300 B2 | 7/2003 | Vibe-Hansen et al. | | 7,217,294 B2 | 5/2007 | Kusanagi et al. |
| 6,599,301 B2 | 7/2003 | Vibe-Hansen et al. | | 7,220,558 B2 | 5/2007 | Luyten et al. |
| 6,599,515 B1 | 7/2003 | Delmotte | | 7,241,316 B2 | 7/2007 | Evans et al. |
| 6,623,963 B1 | 9/2003 | Muller et al. | | 7,252,987 B2 | 8/2007 | Bachalo et al. |
| 6,626,950 B2 | 9/2003 | Brown et al. | | 7,264,634 B2 | 9/2007 | Schmieding |
| 6,630,000 B1 | 10/2003 | Bonutti | | 7,288,406 B2 | 10/2007 | Bogin et al. |
| 6,632,247 B2 | 10/2003 | Boyer, II et al. | | 7,291,169 B2 | 11/2007 | Hodorek |
| 6,652,592 B1 | 11/2003 | Grooms et al. | | 7,297,161 B2 | 11/2007 | Fell |
| 6,652,593 B2 | 11/2003 | Boyer, II et al. | | 7,316,822 B2 | 1/2008 | Binette et al. |
| 6,652,872 B2 | 11/2003 | Nevo et al. | | 7,323,011 B2 * | 1/2008 | Shepard et al. .......... 623/17.11 |
| 6,662,805 B2 | 12/2003 | Frondoza et al. | | 7,323,445 B2 | 1/2008 | Zhang et al. |
| 6,686,184 B1 | 2/2004 | Anderson et al. | | 7,335,508 B2 | 2/2008 | Yayon et al. |
| 6,689,747 B2 | 2/2004 | Filvaroff et al. | | 7,338,492 B2 | 3/2008 | Singhatat |
| 6,696,073 B2 | 2/2004 | Boyce et al. | | 7,338,524 B2 | 3/2008 | Fell et al. |

| | | | |
|---|---|---|---|
| 7,358,284 B2 | 4/2008 | Griffey et al. | |
| 7,361,195 B2 | 4/2008 | Schwartz et al. | |
| 7,365,051 B2 | 4/2008 | Paulista et al. | |
| 7,371,400 B2 | 5/2008 | Borenstein et al. | |
| 7,468,075 B2 | 12/2008 | Lang et al. | |
| 7,468,192 B2 * | 12/2008 | Mizuno et al. | 424/423 |
| 7,479,160 B2 | 1/2009 | Branch et al. | |
| 7,485,310 B2 | 2/2009 | Luyten et al. | |
| 7,488,348 B2 * | 2/2009 | Truncale et al. | 623/23.63 |
| 7,513,910 B2 | 4/2009 | Buskirk et al. | |
| 7,531,000 B2 | 5/2009 | Hodorek | |
| 7,537,617 B2 | 5/2009 | Bindsell et al. | |
| 7,537,780 B2 * | 5/2009 | Mizuno et al. | 424/423 |
| 7,550,007 B2 | 6/2009 | Malinin | |
| 7,563,455 B2 | 7/2009 | McKay | |
| 7,563,769 B2 | 7/2009 | Bogin et al. | |
| 7,601,173 B2 | 10/2009 | Messerli et al. | |
| 7,608,113 B2 | 10/2009 | Boyer, II et al. | |
| 7,621,963 B2 | 11/2009 | Simon et al. | |
| 7,622,438 B1 | 11/2009 | Lazarov et al. | |
| 7,622,562 B2 | 11/2009 | Thorne et al. | |
| 7,628,851 B2 | 12/2009 | Armitage et al. | |
| 7,632,311 B2 | 12/2009 | Seedhom et al. | |
| 7,638,486 B2 | 12/2009 | Lazarov et al. | |
| 7,642,092 B2 | 1/2010 | Maor | |
| 7,648,700 B2 | 1/2010 | Vignery et al. | |
| 7,648,965 B2 | 1/2010 | Vignery et al. | |
| 7,658,768 B2 | 2/2010 | Miller et al. | |
| 7,662,184 B2 | 2/2010 | Edwards et al. | |
| 7,666,230 B2 | 2/2010 | Orban et al. | |
| 2001/0005592 A1 | 6/2001 | Bhatnagar et al. | |
| 2001/0006634 A1 | 7/2001 | Zaleske et al. | |
| 2001/0010023 A1 | 7/2001 | Schwartz et al. | |
| 2001/0011131 A1 | 8/2001 | Luyten et al. | |
| 2001/0016646 A1 | 8/2001 | Rueger et al. | |
| 2001/0018619 A1 | 8/2001 | Enzerink et al. | |
| 2001/0020188 A1 | 9/2001 | Sander | |
| 2001/0021875 A1 | 9/2001 | Enzerink et al. | |
| 2001/0031254 A1 | 10/2001 | Bianchi et al. | |
| 2001/0039457 A1 | 11/2001 | Boyer, II et al. | |
| 2001/0039458 A1 | 11/2001 | Boyer, II et al. | |
| 2001/0043940 A1 | 11/2001 | Boyce et al. | |
| 2001/0051834 A1 | 12/2001 | Frondoza et al. | |
| 2002/0009805 A1 | 1/2002 | Nevo et al. | |
| 2002/0016592 A1 | 2/2002 | Branch et al. | |
| 2002/0035401 A1 | 3/2002 | Boyce et al. | |
| 2002/0042373 A1 | 4/2002 | Carney et al. | |
| 2002/0045940 A1 | 4/2002 | Giannetti et al. | |
| 2002/0055783 A1 | 5/2002 | Tallarida et al. | |
| 2002/0072806 A1 | 6/2002 | Buskirk et al. | |
| 2002/0082704 A1 | 6/2002 | Cerundolo | |
| 2002/0106393 A1 | 8/2002 | Bianchi et al. | |
| 2002/0111695 A1 | 8/2002 | Kandel | |
| 2002/0120274 A1 | 8/2002 | Overaker et al. | |
| 2002/0138143 A1 | 9/2002 | Grooms et al. | |
| 2002/0177224 A1 | 11/2002 | Madry et al. | |
| 2002/0192263 A1 | 12/2002 | Merboth et al. | |
| 2003/0021827 A1 | 1/2003 | Malaviya et al. | |
| 2003/0023316 A1 | 1/2003 | Brown et al. | |
| 2003/0032961 A1 | 2/2003 | Pelo et al. | |
| 2003/0033021 A1 | 2/2003 | Plouhar et al. | |
| 2003/0033022 A1 | 2/2003 | Plouhar et al. | |
| 2003/0036797 A1 | 2/2003 | Malaviya et al. | |
| 2003/0036801 A1 | 2/2003 | Schwartz et al. | |
| 2003/0039695 A1 | 2/2003 | Geistlich et al. | |
| 2003/0040113 A1 | 2/2003 | Mizuno et al. | |
| 2003/0044444 A1 | 3/2003 | Malaviya et al. | |
| 2003/0049299 A1 | 3/2003 | Malaviya et al. | |
| 2003/0050709 A1 | 3/2003 | Noth et al. | |
| 2003/0055502 A1 | 3/2003 | Lang et al. | |
| 2003/0078617 A1 | 4/2003 | Schwartz et al. | |
| 2003/0099620 A1 | 5/2003 | Zaleske et al. | |
| 2003/0144743 A1 | 7/2003 | Edwards et al. | |
| 2003/0229400 A1 | 12/2003 | Masuda et al. | |
| 2003/0236573 A1 | 12/2003 | Evans et al. | |
| 2004/0028717 A1 | 2/2004 | Sittinger et al. | |
| 2004/0033212 A1 | 2/2004 | Thomson et al. | |
| 2004/0039447 A1 | 2/2004 | Simon et al. | |
| 2004/0044408 A1 | 3/2004 | Hungerford et al. | |
| 2004/0062753 A1 | 4/2004 | Rezania et al. | |
| 2004/0102850 A1 | 5/2004 | Shepard | |
| 2004/0115172 A1 | 6/2004 | Bianchi et al. | |
| 2004/0134502 A1 | 7/2004 | Mizuno et al. | |
| 2004/0138748 A1 | 7/2004 | Boyer, II et al. | |
| 2004/0143344 A1 | 7/2004 | Malaviya et al. | |
| 2004/0151705 A1 | 8/2004 | Mizuno et al. | |
| 2004/0166169 A1 | 8/2004 | Malaviya et al. | |
| 2004/0170610 A1 | 9/2004 | Slavin et al. | |
| 2004/0175826 A1 | 9/2004 | Maor | |
| 2004/0192605 A1 | 9/2004 | Zhang et al. | |
| 2004/0193268 A1 | 9/2004 | Hazebrouck | |
| 2004/0197311 A1 | 10/2004 | Brekke et al. | |
| 2004/0197373 A1 | 10/2004 | Gertzman et al. | |
| 2004/0219182 A1 | 11/2004 | Gomes et al. | |
| 2004/0220574 A1 | 11/2004 | Pelo et al. | |
| 2004/0230303 A1 | 11/2004 | Gomes et al. | |
| 2004/0243242 A1 | 12/2004 | Sybert et al. | |
| 2005/0004672 A1 | 1/2005 | Pafford et al. | |
| 2005/0027307 A1 | 2/2005 | Schwartz et al. | |
| 2005/0043814 A1 | 2/2005 | Kusanagi et al. | |
| 2005/0064042 A1 | 3/2005 | Vunjak-Novakovia et al. | |
| 2005/0074476 A1 | 4/2005 | Gendler et al. | |
| 2005/0074481 A1 | 4/2005 | Brekke et al. | |
| 2005/0089544 A1 | 4/2005 | Khouri et al. | |
| 2005/0101957 A1 | 5/2005 | Buskirk et al. | |
| 2005/0112761 A1 | 5/2005 | Halvorsen et al. | |
| 2005/0125077 A1 | 6/2005 | Harmon et al. | |
| 2005/0129668 A1 | 6/2005 | Giannetti et al. | |
| 2005/0152882 A1 | 7/2005 | Kizer et al. | |
| 2005/0159820 A1 | 7/2005 | Yoshikawa et al. | |
| 2005/0159822 A1 | 7/2005 | Griffey et al. | |
| 2005/0196460 A1 | 9/2005 | Malinin | |
| 2005/0209705 A1 | 9/2005 | Niederauer et al. | |
| 2005/0222687 A1 | 10/2005 | Vunjak-Novakovia et al. | |
| 2005/0240281 A1 | 10/2005 | Slivka et al. | |
| 2005/0251268 A1 | 11/2005 | Truncale | |
| 2005/0260612 A1 | 11/2005 | Padmini et al. | |
| 2005/0261681 A9 | 11/2005 | Branch et al. | |
| 2005/0261767 A1 | 11/2005 | Anderson et al. | |
| 2006/0030948 A1 | 2/2006 | Manrique et al. | |
| 2006/0060209 A1 | 3/2006 | Shepard | |
| 2006/0099234 A1 | 5/2006 | Winkler | |
| 2006/0111778 A1 | 5/2006 | Michalow | |
| 2006/0167483 A1 | 7/2006 | Asculai et al. | |
| 2006/0178748 A1 | 8/2006 | Dinger, III et al. | |
| 2006/0200166 A1 | 9/2006 | Hanson et al. | |
| 2006/0210643 A1 | 9/2006 | Truncale et al. | |
| 2006/0216323 A1 | 9/2006 | Knaack et al. | |
| 2006/0216822 A1 | 9/2006 | Mizuno et al. | |
| 2006/0235534 A1 | 10/2006 | Gertzman et al. | |
| 2006/0247790 A1 | 11/2006 | McKay | |
| 2006/0247791 A1 | 11/2006 | McKay et al. | |
| 2006/0251631 A1 | 11/2006 | Adkisson, IV et al. | |
| 2006/0276907 A1 | 12/2006 | Boyer, II et al. | |
| 2007/0014867 A1 | 1/2007 | Kusanagi et al. | |
| 2007/0026030 A1 | 2/2007 | Gill et al. | |
| 2007/0036834 A1 | 2/2007 | Pauletti et al. | |
| 2007/0041950 A1 | 2/2007 | Leatherbury et al. | |
| 2007/0055377 A1 | 3/2007 | Hanson et al. | |
| 2007/0065943 A1 | 3/2007 | Smith et al. | |
| 2007/0067032 A1 | 3/2007 | Felt et al. | |
| 2007/0083266 A1 | 4/2007 | Lang | |
| 2007/0093896 A1 | 4/2007 | Malinin | |
| 2007/0093912 A1 | 4/2007 | Borden | |
| 2007/0098759 A1 | 5/2007 | Malinin | |
| 2007/0100450 A1 | 5/2007 | Hodorek | |

| | | | |
|---|---|---|---|
| 2007/0113951 A1 | 5/2007 | Huang | |
| 2007/0128155 A1 | 6/2007 | Seyedin | |
| 2007/0134291 A1 | 6/2007 | Ting | |
| 2007/0135917 A1 | 6/2007 | Malinin | |
| 2007/0135918 A1 | 6/2007 | Malinin | |
| 2007/0135928 A1 | 6/2007 | Malinin | |
| 2007/0148242 A1 | 6/2007 | Vilei et al. | |
| 2007/0162121 A1 | 7/2007 | Tarrant et al. | |
| 2007/0168027 A1 | 7/2007 | Edwards et al. | |
| 2007/0172506 A1 | 7/2007 | Nycz et al. | |
| 2007/0179607 A1 | 8/2007 | Hodorek et al. | |
| 2007/0185585 A1 | 8/2007 | Bracy et al. | |
| 2007/0276506 A1 | 11/2007 | Troxel | |
| 2007/0029951 A1 | 12/2007 | Davisson et al. | |
| 2007/0299519 A1 | 12/2007 | Schmieding | |
| 2008/0015709 A1 | 1/2008 | Evans et al. | |
| 2008/0027546 A1 | 1/2008 | Semler et al. | |
| 2008/0031915 A1 | 2/2008 | Becerra Ratia et al. | |
| 2008/0038314 A1 | 2/2008 | Hunziker | |
| 2008/0039939 A1 | 2/2008 | Iwamoto et al. | |
| 2008/0039954 A1 | 2/2008 | Long et al. | |
| 2008/0039955 A1 | 2/2008 | Hunziker | |
| 2008/0051889 A1 | 2/2008 | Hodorek | |
| 2008/0065210 A1 | 3/2008 | McKay | |
| 2008/0077251 A1 | 3/2008 | Chen et al. | |
| 2008/0119947 A1 | 5/2008 | Huckle et al. | |
| 2008/0125863 A1 | 5/2008 | McKay | |
| 2008/0125868 A1 | 5/2008 | Branemark | |
| 2008/0138414 A1 | 6/2008 | Huckle et al. | |
| 2008/0154372 A1 | 6/2008 | Peckham | |
| 2008/0167716 A1 | 7/2008 | Schwartz et al. | |
| 2008/0183300 A1 | 7/2008 | Seedhom et al. | |
| 2008/0305145 A1 | 12/2008 | Shelby et al. | |
| 2009/0043389 A1 | 2/2009 | Vunjak-Govakovic et al. | |
| 2009/0069901 A1 | 3/2009 | Truncale et al. | |
| 2009/0069904 A1 | 3/2009 | Picha | |
| 2009/0076624 A1 | 3/2009 | Rahaman et al. | |
| 2009/0099661 A1 | 4/2009 | Bhattacharya et al. | |
| 2009/0117652 A1 | 5/2009 | Luyten et al. | |
| 2009/0131986 A1 | 5/2009 | Lee et al. | |
| 2009/0210057 A1 | 8/2009 | Liao et al. | |
| 2009/0226523 A1 | 9/2009 | Behnam et al. | |
| 2009/0280179 A1 | 11/2009 | Neumann et al. | |
| 2009/0299475 A1 | 12/2009 | Yamamoto et al. | |
| 2009/0312805 A1 | 12/2009 | Lang et al. | |
| 2009/0312842 A1 | 12/2009 | Bursac et al. | |
| 2009/0319051 A9 | 12/2009 | Nycz et al. | |
| 2010/0021521 A1 | 1/2010 | Xu et al. | |
| 2010/0036492 A1 | 2/2010 | Hung et al. | |
| 2010/0036503 A1 | 2/2010 | Chen et al. | |

FOREIGN PATENT DOCUMENTS

| | | | |
|---|---|---|---|
| EP | 0522569 A1 | 1/1993 |
| EP | 0762903 B1 | 6/1995 |
| EP | 0762903 A1 | 12/1995 |
| EP | 0517030 B1 | 9/1996 |
| EP | 5017030 B1 | 9/1996 |
| EP | 0739631 A2 | 10/1996 |
| EP | 0784985 A1 | 7/1997 |
| EP | 0968012 A1 | 9/1998 |
| EP | 1237511 A1 | 6/2001 |
| EP | 1237511 B1 | 6/2001 |
| EP | 1 127 581 A1 | 8/2001 |
| EP | 1 181 908 A1 | 2/2002 |
| EP | 1234552 A1 | 8/2002 |
| EP | 1234555 A2 | 8/2002 |
| EP | 0762903 B1 | 9/2003 |
| EP | 1 181 908 B1 | 12/2003 |
| EP | 0739631 B1 | 12/2003 |
| EP | 1 384 452 A1 | 1/2004 |
| EP | 1234555 A3 | 6/2004 |
| EP | 1 237 511 B1 | 9/2004 |
| EP | 1237511 B1 | 9/2004 |
| EP | 1618178 A1 | 11/2004 |
| EP | 1 127 581 B1 | 6/2005 |
| EP | 1618178 B1 | 1/2006 |
| EP | 1234552 B1 | 8/2006 |
| EP | 0 968 012 B1 | 9/2006 |
| EP | 1 719 531 A2 | 11/2006 |
| EP | 1 719 532 A2 | 11/2006 |
| EP | 1719463 A1 | 11/2006 |
| EP | 1719531 A2 | 11/2006 |
| EP | 1234555 B1 | 2/2007 |
| EP | 0 762 903 B2 | 8/2007 |
| GB | 2102811 A1 | 2/1983 |
| SU | 1454423 A1 | 1/1989 |
| WO | WO 84/04880 A1 | 12/1984 |
| WO | 90/01342 A1 | 2/1990 |
| WO | 93/16739 A1 | 9/1993 |
| WO | WO 94/03584 A1 | 2/1994 |
| WO | 95/25748 A1 | 9/1995 |
| WO | WO 95/33502 A1 | 12/1995 |
| WO | 96/24310 A1 | 8/1996 |
| WO | WO 98/14222 A1 | 4/1998 |
| WO | WO 98/41246 A2 | 9/1998 |
| WO | 98-43686 A1 | 10/1998 |
| WO | WO 99/09914 A1 | 3/1999 |
| WO | WO 99/11298 A2 | 3/1999 |
| WO | 99/15209 A1 | 4/1999 |
| WO | WO 99/21497 A1 | 5/1999 |
| WO | WO 99/22747 A1 | 5/1999 |
| WO | WO 99/48541 A1 | 9/1999 |
| WO | WO 99/52572 A1 | 10/1999 |
| WO | 99/56797 A1 | 11/1999 |
| WO | WO 00/40177 A1 | 7/2000 |
| WO | 00/47114 A1 | 8/2000 |
| WO | 01/07595 A2 | 2/2001 |
| WO | 01/38357 A2 | 5/2001 |
| WO | 01/39788 A2 | 6/2001 |
| WO | 01/46416 A1 | 6/2001 |
| WO | WO 01/43667 A1 | 6/2001 |
| WO | 02/18546 A2 | 3/2002 |
| WO | 02/22779 A2 | 3/2002 |
| WO | 02/36732 A2 | 5/2002 |
| WO | WO 02/058484 A2 | 8/2002 |
| WO | WO 02/064180 A1 | 8/2002 |
| WO | 02/077199 A2 | 10/2002 |
| WO | 02/095019 A1 | 11/2002 |
| WO | 03/007873 A2 | 1/2003 |
| WO | WO 03/007805 A2 | 1/2003 |
| WO | WO 03/007805 A3 | 1/2003 |
| WO | WO 03 007879 A2 | 1/2003 |
| WO | WO 03 007879 A3 | 1/2003 |
| WO | 03/012053 A2 | 2/2003 |
| WO | WO 03/007879 A3 | 8/2003 |
| WO | 03/079985 A2 | 10/2003 |
| WO | 03/087160 A1 | 10/2003 |
| WO | WO 03/007805 A2 | 10/2003 |
| WO | 03/094835 A2 | 11/2003 |
| WO | 03/094835 A3 | 11/2003 |
| WO | 2004/067704 A2 | 8/2004 |
| WO | 2004/069298 A1 | 8/2004 |
| WO | WO 2004/075940 A1 | 9/2004 |
| WO | WO 2004/096983 A2 | 11/2004 |
| WO | WO 2004/096983 A3 | 11/2004 |
| WO | WO 2004/103224 A1 | 12/2004 |
| WO | 2005058207 A1 | 6/2005 |
| WO | WO 2005/110278 A2 | 11/2005 |
| WO | WO 2005/110278 A3 | 11/2005 |
| WO | WO 2006/042311 A2 | 4/2006 |
| WO | WO 2006/042311 A3 | 4/2006 |
| WO | 02/036732 A3 | 9/2006 |
| WO | 2006/113586 A2 | 10/2006 |
| WO | WO 2006/042311 A3 | 11/2006 |
| WO | WO 2007/024238 A1 | 3/2007 |

| | | |
|---|---|---|
| WO | 2006/113586 A3 | 9/2007 |
| WO | 2008/013763 A2 | 1/2008 |
| WO | WO 2008/021127 A2 | 2/2008 |
| WO | 2008/038287 A2 | 4/2008 |
| WO | 2008/013763 A3 | 6/2008 |
| WO | 2008/038287 A3 | 9/2008 |
| WO | WO 2008/106254 A2 | 9/2008 |
| WO | WO 2009/076164 A2 | 6/2009 |
| WO | WO 2009/111069 A3 | 9/2009 |

OTHER PUBLICATIONS

Loeser et al., "Basic Fibroblast Growth Factor Inhibits the Anabolic Activity of Insulin-like Growth Factor 1 and Osteogenic Protein 1 in Adult Human Articular Chondrocytes", Arthritis & Rheumatism, vol. 52, No. 12 (Dec. 2005), pp. 3910-3917.
Kato et al., "Fibroblast Growth Factor is an Inhibitor of Chondrocyte Terminal Differentiation", Journal of Biological Chemistry, vol. 265, No. 10 (Apr. 5, 1990) pp. 5903-5909.
Andrés et al., "A Pro-Inflammatory Signature Mediates FGF2-induced Angiogenesis", Journal of Cellular and Molecular Medicine, (Jun. 28, 2008), available at http://www.ncbi.nlm.nih.gov/pubmed/18624773.
Burger et al., "Fibroblast growth factor receptor-1 is expressed by endothelial progenitor cells", Blood, vol. 100, No. 10 (Nov. 15, 2002) 3527-35.
Baird, "Fibroblast growth factors: activities and significance of non-neurotrophin neurotrophic growth factors", Current Opinions in Neurobiology, (1994) 4:78-86.
Mazué et al., "Preclinical and Clinical Studies with Recombinant Human Basic Fibroblast Growth Factor", Annals New York Academy of Sciences, (1991) 329-340.
Aviles et al., "Testing clinical therapeutic angiogenesis using basic fibroblast growth factor (FGF-2)", British Journal of Pharmacology (2003) 140: 637-646.
http://www.stoneclinic.com/articularcartilagepastegrafting (Copyright 2009).
http://www.technobusiness-solutions.com/article-lyophilization1.html (published Feb. 12, 2002).
Written Opinion issued on Nov. 1, 2004 in connection with International Patent Application No. PCT/US2004/010957.
International Preliminary Report on Patentability issued on Nov. 18, 2005 in connection with International Patent Application No. PCT/US2004/010957.
Written Opinion issued on Apr. 7, 2006 in connection with International Patent Application No. PCT/US2005/030610.
International Preliminary Report on Patentability issued on Feb. 26, 2008 in connection with International Patent Application No. PCT/US2005/030610.
Written Opinion issued on Sep. 21, 2006 in connection with International Patent Application No. PCT/US2005/036878.
International Preliminary Report on Patentability issued on Apr. 17, 2007 in connection with International Patent Application No. PCT/US2005/036878.
International Search Report issued on Jun. 23, 2009 in connection with International Patent Application No. PCT/US2008/051796.
Written Opinion issued on Jun. 23, 2009 in connection with International Patent Application No. PCT/US2008/051796.
International Preliminary Report on Patentability issued on Jul. 28, 2009 in connection with International Patent Application No. PCT/US2008/051796.
International Search Report issued on Jul. 6, 2009 in connection with International Patent Application No. PCT/US2008/085522.
Written Opinion issued on Jul. 6, 2009 in connection with International Patent Application No. PCT/US2008/085522.
International Search Report issued on Jul. 6, 2009 in connection with International Patent Application No. PCT/US2009/001459.
Written Opinion issued on Jul. 6, 2009 in connection with International Patent Application No. PCT/US2009/001459.
Peretti et al., "Biomechanical Analysis of a Chondrocyte-Based Repair Model of Articular Cartilage", Tissue Engineering, Aug. 1, 1999, vol. 5. No. 4, pp. 317-326.

Yee, Cindy J. et al., (2000) Analysis of fibroblast growth factor receptor 3 S249C mutation in cervical carcinoma. Journal of the National Cancer Institute 92(22):1848-1849.
Zhang, Jiandong et al., (1991) Three-dimensional structure of human basic fibroblast growth factor, a structural homolog of interleukin 1 Beta. Proc Natl Acad Sci. USA 88(8):3446-3450.
Zhu, Hengyi et al., (1995) Glu-96 of basic fibroblast growth factor is essential for high affinity receptor binding. Journal of Biological Chemistry 270(37):21869-21874.
Zhu, Hengyi et al., (1997) Analysis of high-affinity binding determinants in the receptor binding epitope of basic fibroblast growth factor. Protein Engineering 10(4):417-421.
Carr, M. E. Jr. and Alving, B. M. (1995) Effect of fibrin structure on plasmin-mediated dissolution of plasma clots. Blood Coag. Fibrinol. 6(6):567-573.
Carr, Marcus E. (1988) Fibrin formed in plasma is composed of fibers more massive than those formed from purified fibrinogen. Thromb. Haemost. 59(3):535-539.
Cook, James L. et al., (2003) Biocompatibility of three-dimensional chondrocyte grafts in large tibial defects of rabbits. Am J Vet Res. 64(1):12-20.
Gao, Jizong et al., (2002) Repair of osteochondral defect with tissue-engineered two- phase composite material of injectable calcium phosphate and hyaluronan sponge. Tissue Engin. Part A 8(5):827-837.
Gruber, Reinhard et al., (2002) Platelets stimulate proliferation of bone cells: involvement of platelet-derived growth factor, microparticles and membranes. Clin Oral Implants Res. 13(5):529-535.
Haisch, A. et al., (2000) Preparation of a pure autologous biodegradable fibrin matrix for tissue engineering. Med Biol Eng Comput. 38(6):686-689.
Itokazu, M. et al., (1997) The sustained release of antibiotic from freeze-dried fibrin-antibioticcompound and efficacies in a rat model of osteomyelitis. Infection 25(6):359-363.
Sims, C. Derek et al., (1998) Tissue engineered neocartilage using plasma derived polymer substrates and chondrocytes. Plastic & Recon. Surg. 101(6):1580-1585.
"Young's Modulus." Entry on http://en.wikipedia.org. accessed Oct. 27, 2005. 3 pages.
Bradford, Marion M. (1976) A Rapid and Sensitive Method for the Quantitation of Microgram Quantities of Protein Utilizing the Principle of Protein-Dye Binding. Analytical Biochemistry 72(1-2):248-254.
Matsuda et al. (1995) In Vivo Chondrogenesis in Collagen Sponge Sandwiched by Perichondrium. J. Biomater. Sci. Polymer Ed., vol. 7, No. 3, pp. 221-229.
Fujisato et al. (1996) Effect of basic fibroblast growth factor on cartilage regeneration in chondrocyte-seeded collagen sponge scaffold. Biomaterials, vol. 17, No. 2, pp. 155-162.
International Preliminary Report on Patentability for PCT/US2009/001459, mailed on May 12, 2010.
Crescenzi et al., "Hyaluronan Linear and Crosslinked Derivatives as Potential/Actual Biomaterials", in Hyaluronan (2002), vol. 1 (Chemical, Biochemical and Biological Aspects), J. F. Kennedy et al., Ed., pp. 261-268.
Michielen et al., "Novel Biomaterials Based on Cross-linked Hyaluronan: Structural Investigations", in Hyaluronan (2002). vol. 1 (Chemical, Biochemical and Biological Aspects), J. F. Kennedy et al., Ed., pp. 269-276.
Aston et al., "Repair of Articular Surfaces by Allografts of Articular and Growth-Plate Cartilage," Journal of Bone and Joint Surgery, Jan. 1986, vol. 68-B, No. 1; pp. 29-35.
Hoffman, "Hydrogels for Biomedical Applications", Advanced Drug Delivery Reviews, 2002, vol. 43, pp. 3-12.
Dahlberg et al., "Demineralized Allogeneic Bone Matrix for Cartilage Repair", Journal of Orthopaedic Research, 1991, vol. 9, pp. 11-19.
Lu et al., "Minced Cartilage without Cell Culture Serves as an Effective Intraoperative Cell Source for Cartilage Repair", Journal of Orthopaedic Research, Jun. 2006, vol. 24, pp. 1261-1270.
Stone et al., "Articular Cartilage Paste Grafting to Full-Thickness Articular Cartilage Knee Joint Lesions: A 2- to 12-Year Follow-up", Arthroscopy: The Journal of Arthoscopic and Related Surgery, Mar. 2006, vol. 22, No. 3, pp. 291-299.
Newman, "Articular Cartilage Repair", American Journal of Sports Medicine, 1998, vol. 26, No. 2, pp. 309-324.
Brittberg et al., "Treatment of Deep Cartilage Defects in the Knee with Autologous Chondrocyte Transplantation", New England Journal of Medicine, Oct. 6, 1994, vol. 331, No. 14 pp. 889-895.
Nixon et al., "Enhanced Repair of Extensive Articular Defects by Insulin-like Growth Factor-I-Laden Fibrin Composites", Journal of Orthopaedic Research, 1999; 17:475-487.
International Cartilage Repair Society, "Cartilage Injury Evaluation Package", www.cartilage.org, 2000.
Richardson et al., "Repair of Human Articular Cartilage After Implantation of Autologous Chondrocytes", Journal of Bone and Joint Surgery [Br], 1999; 81-B:1064-1068.
Brittberg et al., "Autologous Chondrocytes Used for Articular Cartilage Repair: An Update", Clinical Orthopaedics and Related Research, 2001; No. 391 Suppl: S337-S348.
Peterson et al., "Two- to 9-year Outcome After Autologous Chondrocyte Transplantation of the Knee", Clinical Orthopaedics and Related Research, 2000; No. 374: 212-234.
Peterson et al., "Autologous Chondrocyte Transplantation: Biomechanics and Long-term Durability", American Journal of Sports Medicine, 2002, vol. 30, No. 1, pp. 2-12.
Messner et al., "Cartilage Repair: A Critical Review", Acta Orthopaedica Scandinavica, 1996, vol. 67, No. 5, pp. 523-529.
Messner et al., "The long-term Prognosis for Severe Damage to Weight-bearing Cartilage in the Knee: A 14-year Clinical and Radiographic Follow-up in 28 Young Athletes", Acta Orthopaedica Scandinavica, 1996, vol. 67, No. 2, pp. 165-168.
Buckwalter et al., "Articular Cartilage: Degeneration and Osteoarthritis, Repair, Regeneration, and Transplantation", AAOS Instructional Course Lectures, 1998; 47:487-504.
Breinan et al., "Effect of Cultured Autologous Chondrocytes on Repair of Chondral Defects in a Canine Model", Journal of Bone and Joint Surgery [Am], 1997; 79-A:1439-1451.
Breinan et al., "Autologous Chondrocyte Implantation in a Canine Model: Change in Composition of Reparative Tissue with Time", Journal of Orthopaedic Research, 2001; 19:482-492.
Brittberg et al., "Rabbit Articular Cartilage Defects Treated with Autologous Cultured Chondrocytes", Clinical Orthopaedics and Related Research, 1996; 326:270-283.
Nehrer et al., "Chondrocyte-seeded Collagen Matrices Implanted in a Chondral Defect in a Canine Model", Biomaterials, 1998; 19:2313-2328.
Vunjak-Novakovic et al., "Bioreactor Cultivation Conditions Modulate the Composition and Mechanical Properties of Tissue-Engineered Cartilage", Journal of Orthopaedic Research, 1999; 17:130-138.
Bursac, "Collagen Network Contributions to Structure-Function Relationships in Cartilaginous Tissues in Compression" (Dissertation), Boston University College of Engineering, 2002.
Gooch et al., "IGF-I and Mechanical Environment Interact to Modulate Engineered Cartilage Development", Biochemical and Biophysical Research Communications, 2001; 286:909-915.
Pei et al., "Growth Factors for Sequential Cellular De- and Redifferentiation in Tissue Engineering", Biochemical and Biophysical Research Communications, 2002; 294:149-154.
Obradovic et al., "Integration of Engineered Cartilage", Journal of Orthopaedic Research, 19 (6):1089-1097, 2001.
Schaefer et al., "Tissue Engineered Composites for the Repair of Large Osteochondral Defects", Arthritis & Rheumatism, 46(9): 2524-2534 (2002).
Pei et al., "Bioreactors Mediate the Effectiveness of Tissue Engineering Scaffolds", The FASEB Journal, 16:1691-1694, published online (Aug. 7, 2002), 10.1096/fj.02-0083fje.
Madry et al., "Gene Transfer of a Human Insulin-like Growth Factor I cDNA Enhances Tissue Engineering of Cartilage", Human Gene Therapy, 13: 1621-1630 (Sep. 1, 2002).
Pearson et al. (eds.), American Association of Tissue Banks, Standards for Tissue Banking, 2008 (12$^{th}$ ed.), pp. 53-56, 86-88.
International Patent Application No. PCT/US08/85522 filed Dec. 4, 2008 for Cancellous Bone Implant for Cartilage Repair.

International. Patent Application No. PCT/US09/001459 filed Mar. 5, 2009 for Cancellous Constructs, Cartilage Particles and Combinations of Cancellous Constructs and Cartilage Particles.
Osteo Sponge product information, Bacterin International Inc., May 2005.
Nolan et al., "Living Bone Grafts", BMJ, vol. 304, Jun. 13, 1992, pp. 1520 and 1521.
Stone et al., One-Step American Technique of Articular Cartilage Paste Grafting to Traumatic and Arthritic Defects in the Knee Joint (2-7 Years Follow-Up), downloaded from http:web.archive.org/web/20041205005845/http://www.stoneclinic.com/onestep.thm; published Dec. 5, 2004.
Feczko et al., "Experimental Results of Donor Site Filling for Autologous Osteochondral Mosaicplasty", Arthroscopy: The Journal of Arthroscopic and Related Surgery, vol. 19, No. 7 (Sep. 2003), pp. 755-761.
Nettles et al., "Photocrosslinkable Hyaluronan as a Scaffold for Articular Cartilage Repair", Annals of Biomedical Engineering, vol. 32, No. 3, Mar. 2004, pp. 391-397.
Peretti et al., "Cell-Based Bonding of Articular Cartilage: An Extended Study", Journal of Biomedical Materials Research, 64A, 2003, pp. 517-524.
Peretti et al., "Cell-based Tissue-Engineered Allogeneic Implant for Cartilage Repair" Tissue Engineering, 2000, vol. 6. No. 5, pp. 567-576.
Bugbee, "Fresh Osteochondral Allografting", Operative Techinques in Sports Medicine, Apr. 2000, vol. 8, No. 2, pp. 158-162.
Nixon et al., "New Horizons in Articular Cartilage Repair", Proceedings of the Annual Convention of the AAEP, 2001, vol. 47, pp. 217-226.
Girotto et al., "Tissue-specific gene expression in chondrocytes grown on three-dimensional hyaluronic acid scaffolds", Biomaterials, 2003, vol. 24, pp. 3265-3275.
Peretti et al, "A Biomechanical Analysis of an Engineered Cell-Scaffold Implant for Cartilage Repair", Annals of Plastic Surgery, May 2001, vol. 46, No. 5, pp. 533-537.
Hunziker E.B., "Articular Cartilage Repair: Basic Science and Clinical Progress. A Review of the Current Status and Prospects", Osteoarthritis and Cartilage 2001, vol. 10, No. 6, pp. 432-463.
Chen et al., "Repair of Articular Cartilage Defects: Part I. Basic Science of Cartilage Healing", The American Journal of Orthopedics, Jan. 1999, pp. 31-33.
Chen et al., "Repair of Articular Cartilage Defects: Part II. Treatment Options", The American Journal of Orthopedics, Feb. 1999, pp. 88-96.
Buckwalter J.A., "Articular Cartilage Injuries", Clinical Orthopedics and Related Research, 2002, No. 402, pp. 21-37.
Verbruggen et al., "Repair Function in Organ Cultured Human Cartilage. Replacement of Enzymatically Removed Proteoglycans During Longterm Organ Culture", The Journal of Rheumatology, 12:4, (1985), pp. 665-674.
Jackson et al., "Cartilage Substitute: Overview of Basic Science & Treatment Options", Journal of American Academy of Orthopaedic Surgeons, vol. 9 (Jan./Feb. 2001), pp. 37-52.
Office Action mailed on Apr. 19, 2007 in connection with U.S. Appl. No. 11/151,270, filed on Jun. 14, 2005.
Diduch et al., "Joint Repair: Treatment Options for Articular Cartilage Injury", Orthopedic Technology Review (2002) 4:24-27.
Stone et al., "One-Step American Technique of Articular Cartilage Paste Grafting to Traumatic and Arthritic Defects in the Knee Joint (2-7 Years Follow Up)", downloaded from http://www.stoneclinic.com/onestep.htm; publication date unknown, Apr. 4, 2008.
Gilbert, et al., "Decellularization of Tissues and Organs", Biomaterials (2006) 27:3675-3683.
U.S. Appl. No. 12/079,629, filed Mar. 26, 2008 titled Cartilage Implant Plug with Fibrin Glue and Method for Implantation.
Gertzman et al., "A pilot study evaluating sodium hyaluronate as a carrier for freeze-dried demineralized bone powder", Cell and Tissue Banking, vol. 2, 2001, pp. 87-94.
Trzeciak et al., "Evaluation of Cartilage Reconstruction by Means of Autologous Chondrocyte Versus Periosteal Graft Transplantation: An Animal Study", Transplantation Proceedings, vol. 38 (2006), pp. 305-311.

Brighton et al., "Articular Cartilage Preservation and Storage-I. Application of Tissue Culture Techniques to the Storage of Viable Articular Cartilage", Arthritis and Rheumatism, vol. 22, No. 10 (Oct. 1979) pp. 1093-1101.

Mahadev et al., "Autogenous Osteochondral Morselised Grafts for Full Thickness Osteochondral Defects in the Knee Joints of Pigs", Singapore Medical Journal, 2001, vol. 42(9), pp. 410-416.

Hunziker, "Articular Cartilage Structure in Humans and Experimental Animals", *Articular Cartilage and Osteoarthritis*, Raven Press, ed., 1992, pp. 183-199.

Glowacki, "Engineered Cartilage, Bone, Joints and Menisci—Potential for Temporomandibular Joint Reconstruction", Cells Tissues Organs, vol. 169, Issue 3, 2001, pp. 302-308.

Peretti et al., "In Vitro Bonding of Pre-seeded Chondrocyte", Sport Sciences for Health, May 1, 2007, vol. 2, No. 1, pp. 29-33.

Peretti et al., "Biomechanical Analysis of a Chondrocyte-Based Repair Model of Articular Cartilage", Tissue Engineering, Aug. 1, 1999, vol. 5. No. 4, pp. 317-326.

Tsumaki et al., "Role of CDMP-1 in Skeletal Morphogenesis: Promotion of Mesenchymal Cell Recruitment and Chondrocyte Differentiation", J. Cell Biol., Jan. 1999, vol. 144, No. 1, 161-173.

Peretti et al., "Bonding of Cartilage Matrices with Cultured Chondrocytes: An Experimental Model", Journal of Orthopedic Research, Jan. 1998, vol. 16, No. 1, pp. 89-95.

International Patent Application No. PCT/US2008/051796 titled Two Piece Cancellous Construct for Cartilage Repair.

International Search Report issued on Jun. 19, 2006 in connection with International Patent Application No. PCT/US2005/008798.

International Search Report issued on Oct. 28, 2005 in connection with International Patent Application No. PCT/US2004/010956.

International Search Report issued on Nov. 1, 2004 in connection with International Patent Application No. PCT/US2004/010957.

International Search Report issued on Apr. 7, 2006 in connection with International Patent Application No. PCT/US2005/030610.

International Search Report issued on Sep. 21, 2006 in connection with International Patent Application No. PCT/US2005/036878.

Abraham, Judith A. et al., (1986) Human Basic Fibroblast Growth Factor: Nucleotide Sequence And Genomic Organization. EMBO Journal 5(10):2523-2528.

Agrawal, Sudhir et al., (1991) Pharmacokinetics. Biodistribution, And Stability Of Oligodeoxynucleotide Phosphorothioates In Mice. Proc Natl Acad Sci. USA 88(17):7595-7599.

Arakawa, Tsutomu et al., (1993) Production and Characterization of an Analog of Acidic Fibroblast Growth Factor With Enhanced Stability and Biological Activity. Protein Engineering 6(5):541-546.

Bailly, Karine et al., (2000) Uncoupling of cell proliferation and differentiation activities of basic fibroblast growth factor. FASEB Journal 14(2):333-343.

Bange, Johannes et al., (2002) Cancer progression and tumor cell motility are associated with the FGFR4 Arg388 allele. Cancer Research 62(3):840-846.

Bork, Peer (2000) Powers and pitfalls in sequence analysis: The 70% hurdle. Genome Res. 10(4):398-400.

Bork, Peer and Bairoch, Amnon (1996) Go hunting in sequence databases but watch out for the traps. Trends in Genetics 12(10):425-427.

Brenner, Steven E. (1999) Errors in genome annotation. Trends in Genetics 15(4):132-133.

Cappellen, David et al., (1999) Frequent activating mutations of FGFR3 in human bladder and cervix carcinomas. Nature Genetics 23(1):18-20.

Chusho, Hideki et al., (2001) Dwarfism and early death in mice lacking C-type Natriuretic Peptide. Proc Natl Acad Sci. 98(7):4016-4021.

Coughlin, Shaun R. et al., (1988) Acidic and basic fibroblast growth factors stimulate tyrosine kinase activity in vivo. J Biol Chem. 263(2):988-993.

Dell' Accio, Francesco et al., (2001) Molecular markers predictive of the capacity of expanded human articular chondrocytes to form stable cartilage in vivo, Arthritis Rheum. 44(7):1608-19.

Doerks, Tobias et al., (1998) Protein annotation: detective work for function prediction. Trends Genet. 14(6):248-250.

Dvorakova, Dana et al., (2001) Changes in the expression of FGFR3 in patients with chronic myeloid leukaemia receiving transplants of allogeneic peripheral blood stem cells_British Journal Haematology 13(3):832-835.

Eriksson, A. Elisabeth et al., (1991) Three-dimensional structure of human basic fibroblast growth factor. Proc. Natl. Acad. Sci. USA 88:3441-3445 (XP002936511).

Ezzat Shereen et al., (2002) Targeted expression of A Human pituitary tumor-derived isoform of FGF Receptor-4 Recapitulates Pituitary Tumorigenesis. Journal of Clinical Investigation 109(1):69-77.

Faham, Salem et al., (1998) Diversity does make a difference: fibroblast growth factor—Heparin interactions. Curr Opin Struct Biol 8(5):578-586.

Fingl, Edward and Woodbury, Dixon M.(1975) General Principles. In: The Pharmacological Basis of Therapeutics. Fifth edition. Goodman, Louis S. and Gilman, Alfred editors. See also table of contents.

Gargiulo, B. J. et al., (2002) Phenotypic modulation of human articular chondrocytes by bistratene A. Eur Cell Mater. 3:9-18.

Givol, David and Yayon, Avner (1992) Complexity of FGF receptors: genetic basis for structural diversity and functional specificity FASEB J. 6(15):3362-3369.

Hecht, H. J. et al., (2000) Structure of fibroblast growth factor 9 shows a symmetric dimmer with unique receptor-and heparin-binding interfaces. Acta Cryst. D57:378-384.

Johnson, Daniel E. and Williams, Lewis T. (1993) Structural and functional diversity in the FGF receptor multigene family. Adv Cancer Res. 60:1-41.

Kirikoshi, Hiroyuki et al., (2000) Molecular cloning and characterization of Human FGF-20 on chromosome 8p21.3-p22. Biochem Biophys Res Commun. 274(2):337-343.

Kuroda, S. et al., (1999) Anabolic effect of aminoterminally truncated Fibroblast Growth Factor 4 (FGF4) on bone. Bone 25:(4)431-437.

Nakatake, Yuhki et al., (2001) Identification of a novel fibroblast growth factor. FGF-22, preferentially expressed in the inner root sheath of the hair follicle. Biochim Biophys Acta. 1517(3):460-463.

Ngo, J. Thomas et al., (1994) Computational complexity, protein structure prediction, and the Levithal Paradox. In: The Protein Folding Problem and Tertiary Structure Prediction. K. Merz Jr. and S. Le Grand, Editors. 433-506 see also table of contents.

Nishimura, Tetsuya et al., (2000) Identification Of a Novel FGF, FGF-21, Preferentially Expressed In The Liver. Biochim Biophys Acta 1492(1):203-206.

Okada-Ban, Mai et al., (2000) Fibroblast growth factor-2. International Journal of Biochemistry & Cell Biology 32 (3):263-267.

Olsen, Shaun K. (2003) Fibroblast growth factor (FGF) homologous factors share structural but not functional homology with FGFs. J Biol Chem. 278(36):34226-342236.

Ornitz, David M. et al., (1996) Receptor specificity of the fibroblast growth factor family. J Biol Chem. 271(25)1 5292-7.

Ornitz, David M. (2000) FGFs, heparan sulfate and FGFRs: Complex interactions essential for development. Bio Essays 22:108-112.

Pellegrini, Luca et al., (2000) Crystal structure of fibroblast growth factor receptor ectodomain bound to ligand and heparin. Nature 407(6807):1029-1034.

Pillai, Omathanu and Panchagnula, Ramesh (2001) Polymers in drug delivery. Curr Opin Chem Biol 5 (4):447-451.

Plotnikov, Alexander N. et al., (1999) Structural basis for FGF receptor dimerization and activation. Cell 98 (5):641-650.

Plotnikov, Alexander N. et al., (2000) Crystal structures of two FGF-FGFR complexes reveal the determinants of ligand-receptor specificity. Cell 101(4): 413-424.

Sahni, Malika et al., (1999) FGF signaling inhibits chondrocyte proliferation and regulates bone development through the STAT-1 pathway Genes Devel.13(11):1361-1366.

Schlessinger, Joseph et al., (2000) Crystal structure of a ternary FGF-FGFR-1 Heparin complex reveals a dual role for heparin in FGFR binding and dimerization. Mol Cell 6(3):743-750.

Schmal, H. et al., (2007) bFGF influences human articular chondrocyte differentiation. Cytotherapy 9(2):184-93.

Seno, Masaharu et al., (1990) Carboxyl-terminal structure of basic fibroblast growth factor significantly contributes to its affinity for Heparin. Eur J Biochem. 188:239-245.

Shao, Zhang-Qiang et al., (2006) Effects of intramyocardial administration of slow-release basic fibroblast growth factor on angiogenesis and ventricular remodeling in a rat infarct model. Circ. J. 70(4):471-477.

Skolnik, Jeffrey and Fetrow, Jacquelyn S. (2000) From genes to protein structure and function: novel applications of computational approaches in the genomic era. Trends BioTechnol. 18(1):34-39.

Sleeman, Matthew et al., (2001) Identification of a new fibroblast growth factor receptor, FGFR5. Gene 271 (2):171-182.

Smith, Temple and Zhang, Xiaolin (1997) The challenges of genome sequence annotation or The devil is in the details. Nat Biotechnol. 15(12):1222-1223.

Springer, Barry A. et al., (1994) Identification and Concerted Function of Two Receptors Binding Surfaces on Basic Fibroblast Growth Factor Required for Mitogenesis. The Journal of Biological Chemistry 269(43):26879-26884.

Stauber, Deborah J. et al., (2000) Structural interactions of fibroblast growth factor receptor with its ligands. Proc Natl Acad Sci USA 97(1):49-54.

Vajo, Zoltan et al., (2000) The Molecular and Genetic Basis of Fibroblast Growth Factor Receptor 3 Disorders: The Achondroplasia Family of Skeletal Dysplasias, Muenke Craniosynostosis, and Crouzon Syndrome with Acanthosis Nigricans. Endocrine Rev. 21(1):23-39.

Wells, James A. (1990) Additivity of mutational effects in proteins. Biochemistry 29(37):8509-8517.

Yamashita, Tetsuo et al., (2000) Identification of a novel fibroblast growth factor, FGF-23, preferentially expressed in the ventrolateral thalamic nucleus of the brain. Biochemical and Biophysical Research Communications 277 (2):494-498.

Yayon, Avner et al., (1991) Cell surface, heparin-like molecules are required for binding of basic fibroblast growth factor to its high affinity receptor. Cell 64(4):841-848.

Nettles et al., "In Situ Crosslinkable Hyaluronan for Articular Cartilage Repair", 50th Annual Meeting of the Orthopaedic Research Society, Mar. 2004, Paper No. 0202.

* cited by examiner

Fig.1 pH In the supernatents

| day | 2 | 4 | 7 | 9 | 11 | 15 | 18 | 23 | 44 |
|---|---|---|---|---|---|---|---|---|---|
| Ap40 | 7.4 | 7.42 | 7.45 | 7.48 | 7.4 | 7.3 | 7.45 | 7.52 | 7.5 |
| GB14 | 7.55 | 7.52 | 7.5 | 7.48 | 7.4 | 7.48 | 7.48 | 7.5 | 7.52 |
| 46CaO*23TIO2*31P2O5 | 7.4 | 7.5 | 7.5 | 7.4 | 7.4 | 7.4 | 7.38 | 7.41 | 7.41 |
| B0/2 | 7.4 | 7.4 | 7.38 | 7.37 | 7.38 | 7.4 | 7.37 | 7.37 | 7.36 |
| B1/2 | 7.38 | 7.38 | 7.4 | 7.38 | 7.37 | 7.38 | 7.4 | 7.38 | 7.38 |
| B2/2 | 7.37 | 7.4 | 7.39 | 7.4 | 7.4 | 7.39 | 7.4 | 7.39 | 7.37 |
| CaCO3/CaSO4 | 6.7 | 7 | 7.1 | 6.9 | 7 | 6.95 | 6.8 | | |

Fig.2

Calcium In the supernatent (corrected by the calcium content of pure medium)(mmol/l)

| day | 2 | 4 | 7 | 9 | 11 | 15 | 18 | 23 | 44 |
|---|---|---|---|---|---|---|---|---|---|
| Ap40 | 0.02 | 0.43 | 0.63 | 0.49 | 0.47 | 0.68 | 0.87 | 1.38 | 1.68 |
| GB14 | 0.11 | 0.17 | 0.26 | 0.26 | 0.25 | 0.26 | 0.27 | 0.34 | 0.19 |
| 46CaO*23TIO2*31P2O5 | 0.1 | 0.01 | 0.06 | 0.06 | 0.06 | 0.05 | 0.01 | 0.05 | 0.08 |
| B0/2 | 0.02 | 0.02 | 0.04 | 0.06 | 0.06 | 0 | 0 | 0.05 | 0.03 |
| B1/2 | 0.04 | 0.04 | 0.03 | 0.04 | 0.05 | 0.01 | 0.04 | 0.06 | 0.05 |
| B2/2 | 0.06 | 0.03 | 0 | 0.06 | 0.06 | 0.01 | 0.04 | 0.02 | 0.04 |
| CaCO3/CaSO4 | 18.5 | 24.6 | 22.52 | 20.9 | 22.08 | 18.12 | 21.9 | | |

Fig.3

Phosphate the supernatent (corrected by the phosphate content of pure medium)(mmol/l)

| day | 2 | 4 | 7 | 9 | 11 | 15 | 18 | 23 | 44 |
|---|---|---|---|---|---|---|---|---|---|
| Ap40 | 0.12 | 0.07 | 0.02 | 0.06 | 0.08 | 0 | 0 | -0.13 | -0.79 |
| GB14 | 7.28 | 3.68 | 3.04 | 2.84 | 1.9 | 2.98 | 2.17 | 2.92 | 6.25 |
| 46CaO*23TIO2*31P2O5 | 0.12 | 0.05 | 0.19 | 0.22 | 0.17 | 0.2 | 0.15 | 0.18 | 0.27 |
| B0/2 | 0 | 0 | 0.03 | 0.14 | 0.07 | 0.07 | 0.04 | 0.09 | 0.17 |
| B1/2 | 0.14 | 0.14 | 0.14 | 0.14 | 0.16 | 0.13 | 0.17 | 0.17 | 0.17 |
| B2/2 | 0.15 | 0.13 | 0.12 | 0.24 | 0.11 | 0 | 0.09 | 0.07 | 0 |
| CaCO3/CaSO4 | -0.8 | -0.78 | -0.8 | -0.8 | -0.78 | -0.8 | -0.79 | | |

IMPLANT FOR ARTICULAR CARTILAGE REPAIR

RELATED APPLICATIONS

This application claims the benefit of Provisional Application No. 60/697,563, filed Jul. 11, 2005.

STATEMENT REGARDING FEDERALLY SPONSORED RESEARCH OR DEVELOPMENT

Not applicable.

REFERENCE TO SEQUENCE LISTING, A TABLE OR A COMPUTER PROGRAM LISTING COMPACT DISC APPENDIX

None.

FIELD OF INVENTION

The present invention is generally directed towards the treatment of articular cartilage defects using an allograft bone scaffold or carrier. In particular, the allograft bone is treated with allograft chondrocytes to form a cartilage surface on the allograft bone.

BACKGROUND OF THE INVENTION

Chondrocytes are cells specific to articular cartilage. The isolation and cultivation of chondrocytes is a standard procedure, which has been undertaken for more than 10 years. Under two-dimensional culture conditions in cell culture vessels, chondrocytes dedifferentiate to fibroblast-like cells. During the dedifferentiation they lose their typical properties (grade of differentiation, cell form, synthesis of cartilage-specific matrix components), which are essential for physiology and biomechanics of cartilage.

For many years there have been attempts to transplant dedifferentiated chondrocytes grown under two-dimensional culture conditions into human joint defects. Transplantation of cells grown in culture provides another method of introducing a new cell population into chondral and osteochondral defects. The procedure uses arthroscopy to take a biopsy from a healthy, less loaded area of articular cartilage. Enzymatic digestion of the harvested tissue releases the cells that are sent to a laboratory where they are grown. Once cultivated, they are injected during a more open and extensive knee procedure into areas of defective cartilage in an attempt to facilitate the repair of damaged tissue.

The technique of autologous chondrocyte transplantation is very complex and requires postoperative immobilization of the patient. The surgical site cannot bear load post surgery because the transplanted chondrocytes have to reach their original biological state (redifferentiation of in vitro dedifferentiated cells), then have to anchor to the defect, synthesize the cartilage-specific matrix and rebuild a new cartilage.

In the procedure of mosaicplasty (autologous cartilage transplantation), cartilage-bone cylinders are removed from non-load-bearing joint areas of the patient and transplanted into the defect. This method shows good clinical results including a good load capacity of the operated knee-joint, but is only applicable to small cartilage defects due to the limited availability of autologous osteochondral cylinders. Classical operation techniques, which do not use cartilage or chondrocyte transplantation (abrasion, debridement, Pridie-drilling), result only in a defect repair with fibrous, less load-bearing tissue unfortunately. Additionally, repeated treatment is necessary as this tissue degenerates over time.

Osteochondral transplantation or mosaicplasty involves excising all injured or unstable tissue from the articular defect and creating cylindrical holes in the base of the defect and underlying bone. These holes are filled with autologous cylindrical plugs of healthy cartilage and bone in a mosaic fashion. The osteochondral plugs are harvested from a lower weight-bearing area of lesser importance in the same joint. Reports of results of osteochondral plug autografts in a small number of patients indicate that they decrease pain and improve joint function, however, long-term results have not been reported. Factors that can compromise the results include donor site morbidity, effects of joint incongruity on the opposing surface of the donor site, damage to the chondrocytes at the articular margins of the donor and recipient sites during preparation and implantation, and collapse or settling of the graft over time. The limited availability of sites for harvest of osteochondral autografts restricts the use of this approach to treatment of relatively small articular defects and the healing of the chondral portion of the autograft to the adjacent articular cartilage remains a concern.

As previously noted, transplantation of cells grown in culture provides another method of introducing a new cell population into chondral and osteochondral defects. Carticel® is a commercial process to culture the patient's own cartilage cells for use in the repair of cartilage defects in the knee joint marketed by Genzyme Biosurgery in the United States and Europe. The procedure uses arthroscopy to take a biopsy from a healthy, less loaded area of articular cartilage. Enzymatic digestion of the harvested tissue releases the cells that are sent to a laboratory where they are grown for a period ranging from 2-5 weeks to achieve a 10 fold increase in cell mass. Once cultivated, the autologous cells are injected during an open and extensive knee procedure into areas of defective cartilage where it is hoped that they will facilitate the repair of damaged tissue. An autologous periosteal flap with cambium layer facing down is used to seal the transplanted cells in place and act as a mechanical barrier. Fibrin glue is used to seal the edges of the flap. This technique preserves the subchondral bone plate. Proponents of this procedure report that it produces satisfactory results, including the ability to return to demanding physical activities, in more than 80% of patients and that biopsy specimens of the tissue in the graft sites show hyaline-like cartilage repair. However, long term studies of this procedure in rabbits and dogs showed limited success and showed degradation at the implant site. The original study report has been criticized for not being a prospective controlled randomized study and for lack of quantitative or mechanical data. Of interest, a 14 year follow-up of a similar patient group that underwent diagnostic arthroscopy in combination with one of several treatments (removal of bone bodies, shaving, Pridie drilling) had good to excellent knee function in 78% of the patients. Thus, further studies are needed to assess the function and durability of the new tissue to determine whether it improves joint function and delays or prevents joint degeneration.

As with the perichondral graft, patient/donor age may compromise the success of this procedure as the chondrocyte population decreases with increasing age. Disadvantages to this procedure include the need for two separate surgical procedures, potential damage to surrounding cartilage when the periosteal patch is sutured in place, the requirement of demanding microsurgical techniques, and the expensive cost of the procedure which is currently not covered by insurance.

The use of implants for cartilage defects is much more limited than that for bone defects. Aside from the fresh allograft implants and autologous implants, U.S. Pat. No. 6,110,209 issued Nov. 5, 1998 shows the use of an autologous articular cartilage cancellous bone paste to fill arthritic defects. The surgical technique is arthroscopic and includes debriding (shaving away loose or fragmented articular cartilage), followed by morselizing the base of the arthritic defect with an awl until bleeding occurs. An osteochondral graft is then harvested from the inner rim of the intercondylar notch using a trephine. The graft is then morselized in a bone graft crusher, mixing the articular cartilage with the cancellous bone. The paste is then pushed into the defect and secured by the adhesive properties of the bleeding bone. The paste can also be mixed with a cartilage stimulating factor, a plurality of cells, or a biological glue. All patients are kept non-weight bearing for four weeks and used a continuous passive motion machine for six hours each night. Histologic appearance of the biopsies have mainly shown a mixture of fibrocartilage with hyaline cartilage. Concerns associated with this method are harvest site morbidity and availability, similar to the mosaicplasty method.

U.S. Pat. No. 6,379,367 issued Apr. 30, 2002 discloses a plug with a base membrane, a control plug, and a top membrane which overlies the surface of the cartilage covering the defective area of the joint.

U.S. Pat. No. 6,488,033 issued Dec. 3, 2002 discloses an allograft plug with a cartilage cap which is surface contour matched to the surface of a condyle defect area which is to be replaced. The allograft plug is transplanted in an interference fit within the cavity site which remains after a condylar defect is removed from a patients condyle.

The present implant and method differs from the above prior art in that it is directed to allograft chondrocyte transplantation on an allograft cancellous bone carrier to provide an implant for cartilage transplantation.

SUMMARY OF TH INVENTION

The present method utilizes techniques of autograft and/or allograft chondrocyte transplantation onto a demineralized allograft cancellous bone implant structure to form an implant with a cartilage layer on the bone structure for use in cartilage repair on a patient at a later time.

It is an object of the invention to use allograft cancellous bone as a carrier on which to grow a cartilage layer for use in cartilage repair.

It is an object of the invention to provide an autograft and/or allograft implant for joints which provides pain relief, restores normal function and will postpone or alleviate the need for prosthetic replacement.

It is also an object of the invention to provide a cartilage repair implant which is easily placed in a defect area by the surgeon using an arthroscopic, minimally invasive technique.

It is further an object of the invention to provide an allograft implant procedure which is applicable for both partial and full thickness lesions.

It is yet another object of the invention to provide a cartilage implant which can be uniformly used for any patient.

These and other objects, advantages, and novel features of the present invention will become apparent when considered with the teachings contained in the detailed disclosure along with the accompanying drawings

BRIEF DESCRIPTION OF THE DRAWINGS

FIG. 1 is a chart showing pH in the supernatants through a 44 day period;

FIG. 2 is a chart showing calcium in the supernatants corrected by the calcium content of pure medium through a 44 day period; and FIG. 3 is a chart showing phosphate in the supernatant corrected by the phosphate content of pure medium through a 44 day period.

DETAILED DESCRIPTION OF TH INVENTION

The present invention is susceptible of embodiment in various forms as will hereinafter be described with the understanding that the present disclosure is to be considered as an exemplification of the invention, and is not intended to limit the invention to the specific embodiments disclosed herein.

Sterile cancellous bone replacement structures were utilized for the in vitro grown cartilage replacements, which allow the fabrication of load-bearing constructs. Bone morphogenetic proteins ("BMP's") from the cancellous bone plugs have a positive effect on chondrocyte differentiation in vitro by stimulating the formation of a native, chondrocyte-phenotype and proper matrix production by the cells. The highest stimulation effect of BMP's on chondrocytes can be observed, if BMP's are immobilized onto a carrier or retained in a biological matrix. In these carriers the natural BMP's of the bone are released by the demineralization but retained in the carrier matrix. For evaluating the effect of the biological carrier structure of cancellous bone on chondrocyte growth, different synthetic carrier materials were used, among them GB 14 ($Ca_2KNa(PO_4)_2$), ceramics and hydroxyapatite.

In order to develop the in vitro manufactured cartilage constructs, chondrocytes were isolated from cartilage samples taken from donors by enzymatic digestion with collagenase, DNAse and hyaluronidase. Since the total number of chondrocytes and cell proliferation decrease with donor age, only donors younger than 50 years were used. Furthermore, bones having joint diseases and bone fractures were excluded from donor selection. After the enzymatic digestion, a suspension of chondrocytes was obtained and tested by trypan blue exclusion to determine the viability of the cell suspension. The suspension was seeded to standard cell culture vessels in order to expand the cells. Since serum is necessary for a good chondrocyte growth and maturation, the medium used contained 10% fetal calf serum. Ascorbic acid was added to stimulate the collagen production by the cells.

The redifferentiation potential of two-dimensionally expanded cells was tested by transferring them into a three-dimensional agarose gel. During expansion, the cells lost their original phenotype, forming fibroblast-like cells. After transferring them into the agarose gel, the normal, round chondrocyte phenotype could be observed, indicating that the cells were able to redifferentiate. The chondrocytes were resuspended in 0.5% low melting agarose reaching a final density of 2 million cells/ml in order to increase the attachment on the carriers and was then seeded onto the following different carrier materials.

I. Evaluation of Different Carrier Materials for Chondrocyte Cultures

The following synthetic carriers (bone replacement materials) were investigated:

a1) $CaCO_3/CaSO_4$ a2) Ap40 (Apatite), slurry 6.89 μm a3) GB 14 a4) 46 $CaO*23TiO_2*31P_2O_5$

The following biologic carriers were evaluated (human cancellous bone, frozen, sterilized with peracetic acid, provided by the tissue bank of DIZG)

b1) B0/1, donor 432/98, 54 y., cancellous bone from tibia plateau not demineralized b2) B1/1 totally demineralized b3) B2/1 superficially(surface) demineralized b4) B0/2 donor 432/98, 54 y., cancellous bone from femur epiphysis not demineralized b5) B1/2 totally demineralized b6) B2/2 superficially(surface) demineralized b7) C0/2 donor 430/98, 60 y., cancellous bone from vertebral column not demineralized b8) C1/2 totally demineralized b9) C2/2 superficially(surface) demineralized The demineralization process was done according to standard operations for demineralization of cancellous bone. The cancellous cubes were washed in order to remove the cells and then dried at 37° C. for 36 hours. The cubes (1 cm×1 cm×1 cm) were demineralized in 1 N HCl for 24 hours at room temperature. For the totally demineralized cubes, the whole cancellous bone cube was incubated in this solution. In the case of the partially demineralized bone only the front surface of the cube was immersed to 2 mm depth in the solution. Approximately 2 mm of the surface of the cube was totally demineralized with a boundary layer between the fully demineralized section and the mineralized section being about 50 µm thick. Afterwards the cubes were washed with sterile water for injection until the pH was neutral.

II. Macroscopic and Microscopic Evaluation of the Carriers

The $CaCO_3/CaSO_4$ (a1) carrier showed a rough surface that could be easily destroyed if touched with forceps. All other materials Ap40, GB 14 and 46 $CaO*23TiO_2*31P_2O_5$ had a plain and stiff surface, which was not destroyed during manipulation. All synthetic carriers were sterilized prior to use at 186° C./2.5 hours.

The totally and superficially demineralized cancellous bones cubes (b1-9) also showed no differences in material resistance (resistance investigated by test with forceps, qualitative evaluation). Both materials had a soft and spongy appearance.

Large pores in the range of 10-100 µm were observed in all cancellous samples (b1-9) during microscopic evaluation. The pore size represented a multiple of the cell volume of a chondrocyte. Samples obtained from vertebral column had a lower pore size than all other preparations. However, no particular bone tissue; namely, tibia, femur, vertebral column appeared to have superior or inferior chondrocyte growth capacities to the other.

III. Long-Term Incubation of the Carrier Materials

Both synthetic and allograft cancellous carriers were incubated under cell culture conditions in order to evaluate their long-term stability (incubation in Ham's F12 medium at 37° C., 6 weeks, no addition of cells). The pH as well as the calcium and phosphate concentrations were measured in the supernatants every third day.

No structural changes were detected after the 6 week incubation of Ap40 (a2) and 46 $CaO*23TiO_2*31P_2O_5$ (a4). White, crystalline sediments were observed in the medium after 44 days of incubation from the carrier GB 14. The $CaCO_3/CaSO_4$ carrier exhibited dramatic structural changes and volume reduction under incubation at cell culture conditions. The process of material destruction started after 3 days of incubation and was accompanied by a large amount of particle release into the medium.

A medium pH of 7.32 was measured during long-term incubation of $CaCO_3/CaSO_4$ carrier. The long term incubation only lasted 16 days as no further incubation was possible because of degradation of carrier. In supernatants of GB 14, the carriers had a relatively high pH of more than 7.5 (7.52) detected after 44 days. In the case of 46 $CaO*23TiO_2*31P_2O_5$-ceramic a pH of 7.5 was determined at days 4 and 7 followed thereafter by only physiological pH-values (pH 7.4). Supernatants of Ap40 showed a physiological pH during the entire investigation increasing to 7.5 after 44 days.

A release of calcium into the medium was observed during incubation of $CaCO_3/CaSO_4$, Ap40 and GB 14 carriers (calcium release of $CaCO_3/CaSO_4$>Ap40>GB 14). Additionally, high amounts of phosphate were detected in supernatants from GB 14 carriers with an increase in phosphate in 46 $CaO*23TiO_2*31P_2O_5$ carriers.

Carriers that release particles are not suited for transplantation into the knee joint because of the potential induction of cartilage damage and joint dysfunction. Also, carriers with high disposal of calcium and phosphate are not useful because they may induce undesired chondrocyte calcification. Consequently, only Ap40 and 46 $CaO*23TiO_2*31P_2O_5$ were used as non-biological carriers for establishing three-dimensional chondrocyte cultures.

After 6 weeks of incubation of the biological carriers (cancellous bone tissue forms), there was no evidence of structural changes, volume reduction or release of calcium or phosphate. Only physiological pH values (pH 7.4) were measured in the supernatants during long-term incubation of the cancellous bone samples. All biological carriers did not release significant amounts of calcium or phosphate to the medium. There were no significant pH changes observed if the bone cubes were submitted to along term incubation in medium and the final pH reached physiological values of approximately pH 7.4 after 44 days of incubation.

IV. Isolation and Cultivation of Human Chondrocytes

Human chondrocytes were isolated by enzymatic digestion of human articular cartilage (donor age <50 years, no degenerative defects of the knee joint, no fractures of the underlying bone). A high cell viability of >90%, in many cases 100% was measured after the isolation.

The cells were cultivated in medium without further supplementation with growth factors. The medium was changed every third day. A good cell adhesion on the cultures vessels (cell culture flasks) was observed after 7 days of incubation at 37° C. and 5% $CO_2$. Growth kinetics showed that the population doubling time as well as the lag time were increased with increasing passage of the cells. The chondrocytes showed a dedifferentiated, fibroblast-like phenotype in two-dimensional culture.

The redifferentiation potential of the dedifferentiated chondrocytes was evaluated in 3D agarose cultures where the typical round cell form was observed (original chondrocyte phenotype, sign of redifferention of dedifferentiated cells).

V. Development of Three-Dimensional Chondrocyte Cultures

The different carriers were fixed to the culture vessels (24 well plates) by sealing with 4% low melting agarose. The surfaces of the carriers were prepared for cell seeding by coating with poly-L-lysine (incubation 1 hour, non-bound lysine removed by washing). The chondrocytes taken from both live and deceased donors were resuspended in 2% low melting agarose and incubated in the refrigerator for 7 minutes in order to obtain a more viscous suspension. The top of each carrier was overlaid with this viscous cell suspension. The seeded carriers were then transferred into the refrigerator for 15 minutes to allow for gelation. This was followed by a 1-hour incubation in the incubator (37° C., 5% $CO_2$). Afterwards, each vessel was supplied with culture medium. All cultures were incubated for 40 days and the medium was changed every third day.

Because of the low material stability of all other synthetic materials only Ap40 and 46 $CaO*23TiO_2*31P_2O_5$-ceramic were used for the establishment of three-dimensional chondrocyte cultures. Ap40 showed a pH increase as well as increases in calcium in the supernatent. 46 $CaO*23TiO_2*31P_2O_5$ showed an increase in the phosphate in the supernatant. Fibroblast-like, dedifferentiated cells were observed at the surfaces of these materials after 15 days incubation, however, the majority of the surface was not covered by cells. The cells formed only a single layer and were not surrounded by significant amounts of extracellular matrix. The amount of cells did not increase in the following culture period and there was no macroscopic sign of neocartilage formation on these carriers.

There was a significant colonization of the osteobiological carriers (cancellous bone) with chondrocytes detectable after 40 days incubation. The range of cell density (i.e., cells per ml, or cells per $cm^3$) will provide attachment on the osteobiological carrier in a range from between 0.2 to 10 million cells per ml, or cells per $cm^3$. The cells showed a chondrocyte-like, round appearance. The chondrocytes covered the entire carrier surface and were surrounded by significant amounts of extracellular matrix. A multi-layer growth and formation of cell clusters could be detected. The multilayer chondrocyte growth was about 4 layers high forming a cartilage layer approximately 2.0 mm thick with a cell density of approximately 10 million cells per $cm^3$. This compares to the thickness of articular cartilage which is 2-5 mm. In articular cartilage, the chondrocytes are not arranged in multilayers, but in stacks of 1 to 8 cells, and the cellularity per amount of tissue is lower. In the case of partially demineralized cancellous carriers, a neo-cartilage formation could be observed macroscopically by appearance of a white opalescent capsule which was stable if impressed with forceps. In all other carriers this capsule formation was not noticeable macroscopically.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

We claim:

1. An implant for articular cartilage repair, comprising a three-dimensional body formed of cancellous bone and having a demineralized section formed by demineralization, the demineralized section containing bone morphogenetic proteins (BMP's) that are released by the demineralization but retained in said body, and a cartilage layer formed on a surface of the demineralized section, said cartilage layer being formed by a method including the steps of:

(a) isolating chondrocytes from articular cartilage of a donor;
   (b) cultivating the isolated chondrocytes in a medium;
   (c) suspending the cultivated chondrocytes in agarose;
   (d) adding the cultivated chondrocytes to the demineralized section of said body, whereby the cultivated chondrocytes are stimulated by the BMPs retained in said body; and
   (e) incubating the cultivated chondrocytes to form a plurality of layers of chondrocytes on the demineralized section, wherein the plurality of layers of chondrocytes forms said cartilage layer.

2. The implant as claimed in claim 1, wherein the chondrocytes are allograft chondrocytes.

3. The implant as claimed in claim 2, wherein the donor is less than 50 years of age.

4. The implant as claimed in claim 2, wherein the donor is alive.

5. The implant as claimed in claim 2, wherein the donor is deceased.

6. The implant as claimed in claim 1, wherein the demineralized section has a depth of approximately 2 mm.

7. The implant as claimed in claim 6, wherein said body includes a mineralized section and a boundary layer formed between the demineralized section and the mineralized section, the boundary layer having a thickness of about 50 microns.

8. The implant as claimed in claim 1, wherein said body includes pores having a size that ranges from 10 to 100 microns.

9. The implant as claimed in claim 1, wherein step (b) includes expanding the chondrocytes in a two-dimensional culture until the chondrocytes are dedifferentiated.

10. The implant as claimed in claim 1, wherein step (e) is performed until said cartilage layer has a thickness of approximately 2.0 mm.

11. The implant as claimed in claim 1, wherein the plurality of layers of chondrocytes includes four layers.

12. The implant as claimed in claim 1, wherein the chondrocytes are autograft chondrocytes.

13. The implant as claimed in claim 1, wherein said body is formed of allograft cancellous bone.

14. The implant as claimed in claim 1, wherein step (b) includes placing the surface of the demineralized section in a culture vessel and preparing the surface of the demineralized section for cell seeding by coating the surface with poly-L-lysine.

15. The implant as claimed in claim 1, wherein step (e) is performed until said cartilage layer has a thickness in a range of from 2 mm to 5 mm.

16. The implant as claimed in claim 1, wherein said body includes pores having a size that represents a multiple of the cell volume of a chondrocyte.

17. The implant as claimed in claim 1, wherein step (e) is performed for a period of at least 40 days.

18. The implant as claimed in claim 1, wherein the cell density of the chondrocytes in said cartilage layer is about 10 million cells per $cm^3$.

19. The implant as claimed in claim 1, wherein all of said body is demineralized.

* * * * *